US010264784B2

(12) United States Patent
Wilson

(10) Patent No.: US 10,264,784 B2
(45) Date of Patent: Apr. 23, 2019

(54) INSTRINSICALLY ANTIMICROBIAL POROSIC MATRIX COMPOSITES AND METHOD OF MANUFACTURE THEREOF

(71) Applicant: John Paul Wilson, Huntington, NY (US)

(72) Inventor: John Paul Wilson, Huntington, NY (US)

( * ) Notice: Subject to any disclaimer, the term of this patent is extended or adjusted under 35 U.S.C. 154(b) by 0 days.

(21) Appl. No.: 15/554,681

(22) PCT Filed: Mar. 7, 2016

(86) PCT No.: PCT/US2016/021250
§ 371 (c)(1),
(2) Date: Aug. 30, 2017

(87) PCT Pub. No.: WO2016/144907
PCT Pub. Date: Sep. 15, 2016

(65) Prior Publication Data
US 2018/0077925 A1 Mar. 22, 2018

Related U.S. Application Data

(60) Provisional application No. 62/129,522, filed on Mar. 6, 2015.

(51) Int. Cl.
*C08J 9/00* (2006.01)
*C08J 9/26* (2006.01)
(Continued)

(52) U.S. Cl.
CPC .............. *A01N 25/16* (2013.01); *A01N 25/10* (2013.01); *A01N 59/16* (2013.01); *A01N 59/20* (2013.01); *A47L 13/17* (2013.01); *A47L 13/51* (2013.01); *C08J 9/0004* (2013.01); *C08J 9/0014* (2013.01); *C08J 9/0066* (2013.01); *C08J 9/26* (2013.01); *C08J 9/40* (2013.01); *C08K 3/08* (2013.01);
(Continued)

(58) Field of Classification Search
CPC ........ A01N 25/10; A01N 25/16; A01N 59/16; A01N 59/02; B01D 2325/026; B29L 2031/7406; B22F 3/11; B22F 3/114
See application file for complete search history.

(56) References Cited

U.S. PATENT DOCUMENTS

2008/0268019 A1* 10/2008 Badylak .............. A61L 27/3633
424/426
2008/0305027 A1* 12/2008 Johnston ................ B01D 53/02
423/339

FOREIGN PATENT DOCUMENTS

EP 2848172 * 11/2014

* cited by examiner

*Primary Examiner* — Stella K Yi
(74) *Attorney, Agent, or Firm* — Ping Wang; Morris, Manning & Martin, LLP

(57) ABSTRACT

A method of manufacturing a flexible intrinsically antimicrobial absorbent porosic composite controlling for an effective pore size using removable pore-forming substances and physically incorporated, non-leaching antimicrobials. A flexible intrinsically antimicrobial absorbent porosic composite controlled for an effective pore size composited physically incorporated, high-surface area, non-leaching antimicrobials, optionally in which the physically incorporated non-leaching antimicrobial exposes nanopillars on its surface to enhance antimicrobial activity. A kit that enhances the effectiveness of the intrinsically antimicrobial absorbent porosic composite by storing the composite within an antimicrobial container.

12 Claims, 6 Drawing Sheets

(51) Int. Cl.
  *C08J 9/40*   (2006.01)
  *C08K 3/08*   (2006.01)
  *A01N 25/10*  (2006.01)
  *A01N 25/16*  (2006.01)
  *A01N 59/16*  (2006.01)
  *A01N 59/20*  (2006.01)
  *A47L 13/17*  (2006.01)
  *A47L 13/51*  (2006.01)

(52) U.S. Cl.
  CPC .... *C08J 2201/036* (2013.01); *C08J 2201/038* (2013.01); *C08J 2201/046* (2013.01); *C08J 2201/0422* (2013.01); *C08J 2201/0444* (2013.01); *C08J 2205/06* (2013.01); *C08J 2207/00* (2013.01); *C08J 2207/12* (2013.01); *C08J 2300/24* (2013.01); *C08J 2301/02* (2013.01); *C08J 2301/24* (2013.01); *C08J 2321/00* (2013.01); *C08J 2355/02* (2013.01); *C08K 2003/085* (2013.01); *C08K 2003/0806* (2013.01)

INSTRINSICALLY ANTIMICROBIAL POROSIC MATRIX COMPOSITES AND METHOD OF MANUFACTURE THEREOF

This application claims priority from U.S. Provisional Application No. 62/129,522, filed Mar. 6, 2015, which is incorporated herein by reference.

FIELD

The present application relates generally to the field of products especially porosic matrix composites useful for absorption and cleaning which function while providing continual protection from bacteria and other harmful environmental pathogens.

BACKGROUND

Many products are exposed to, or even create, conditions in which microbes can grow. These conditions include the presence of water or moisture, the presence of biological material capable of serving as microbe food and frequently the presence of air. (It is noted that anaerobic microbes also exist.) These conditions are especially prevalent in products used in cleaning and for absorption. For example, in sponges, commonly used for cleaning, the presence of air (from its pores), water (from use) and food (from its use in cleaning) combine to turn the cleaning device into a microbe incubator. Indeed, in NSF International studies (formerly the National Sanitary Foundation), the kitchen sponge contains >99% of bacteria in all locations sampled within the home (Robert S. Donofrio R S, Bechanko R, Hitt N, O'Malley K, Charnauski T, Bestervelt L L, Saha R, Saha N. Are We Aware of Microbial Hotspots in Our Household? Journal of Environmental Health 2010) and between 45% and 100% of sponges are infected with antibiotic resistant bacteria (B M Marshall. The frequency of antibiotic-resistant bacteria in homes differing in their use of surface antibacterial agents. *Current Microbiology* 65(4):407-15, 2012; Hernandez, Jaime M. *Antibiotic-resistant and pathogenic bacteria in kitchen sponges.* Dissertation, Quinnipiac University, 174 pages, 2014). Similar situations exist in many other applications such as cleaning brushes, dishcloths, sponge cloths and mops.

Attempts to date to address this problem have centered predominantly around spray-on microbiostatic agents which slow the growth of microbes. Such chemicals, most commonly quaternary amines, are often toxic, including to aquatic life where wastewater from cleaning ends up. Indeed quaternary amines are classified as "asthmagens" or chemical that causes asthma by The Association of Occupational and Environmental Clinics (See Table 1 and "Don't Wipe Out: The Hidden Hazards Of Antibacterial Wipes." EWG Enviroblog. Sep. 21, 2012. Accessible at www.ewg.org/enviroblog/2012/09/dont-wipe-out-hidden-hazards-antibacterial-wipes). Just as importantly, these chemicals have no attachment to the underlying sponge material and are steadily dissolved by water over time. Once they are sufficiently leached out, cleaning articles are thus turned into microbe- and pathogen-incubators and spreaders.

There thus exists a need for antimicrobial products, in particular those used in cleaning with absorptive and wiping qualities such as a sponge, which have antimicrobial properties to prevent the creation and spread of contamination, especially contamination with microbes and pathogens, which maintain those properties over time even in the presence of materials they have absorbed, including microbes, pathogen and foodstuffs, and which do not leach antimicrobial agents over time and are thus health- and environmentally-friendly. The present application provides an effective means of cost-effectively manufacturing such products typically used in cleaning and decontaminating surfaces like those in kitchens or other household areas which may contribute to the spread of harmful microbes. Further aspects and advantages of the application will appear from the following description taken together with the accompanying drawings.

TABLE 1

| AOEC Exposure Code | Primary Name | Synonym | A = Asthmagen | RS = Asthma Sensitizer | Registry of Toxic Effects of Chemical Substances (RTECS) number | CAS number |
| --- | --- | --- | --- | --- | --- | --- |
| 322.321 | Benzalkonium Chloride | Benzalkonium Chloride | A | Rs | BO3150000 | 8001-54-5 |
| 322.321 | Benzyl-C10-16-alkyldimethyl, chlorides | Benzyl-C10-16-alkyldimethyl, chlorides | A | Rs | BO3150000 | 68989-00-4 |
| 322.3211 | BTC 927 | BTC 927 | A | Rs | BO3150000 | 8045-22-5 |
| 322.3212 | Dialkyl Methyl Benzyl Ammonium Chloride | Dialkyl Methyl Benzyl Ammonium Chloride | A | Rs | | 73049-75-9 |
| 322.3213 | Dimethyl Ethyl Benzyl Ammonium Chloride | Dimethyl Ethyl Benzyl Ammonium Chloride | A | Rs | | 68956-79-6 |
| 322.3214 | Benzyldimethylstearyl-ammonium Chloride | Benzyldimethylstearyl-ammonium Chloride | A | Rs | BO3150000 | 122-19-0 |
| 322.322 | Dodecyl-dimethyl-benzylammonium Chloride | Dodecyl-dimethyl-benzylammonium Chloride | A | Rs | BO6821500 | 139-07-1 |
| 322.322 | Dodecyl-dimethyl-benzylammonium Chloride | Lauryl Dimethyl Benzyl Ammonium Chloride | A | Rs | BO6821500 | 139-07-1 |
| 322.323 | Didecyl Dimethyl Ammonium Chloride | Didecyl Dimethyl Ammonium Chloride | A | Rs | BO6821500 | 7173-51-5 |
| 322.324 | Cetalkonium Chloride | Cetalkonium Chloride | A | Rs | BO3150000 | 122-18-9 |
| 322.325 | BTC 776 | BTC 776 | A | Rs | BO3150000 | 53516-76-0 |
| 322.326 | Alkyl Dimethyl Benzyl Ammonium Chloride | Alkyl Dimethyl Benzyl Ammonium Chloride | A | Rs | BO3150000 | 61789-71-7 |
| 322.327 | Benzyl-C12-18-alkyldimethyl, chlorides | Benzyl-C12-18-alkyldimethyl, chlorides | A | Rs | BO3150000 | 68391-01-5 |
| 322.328 | Benzyl-C12-16-alkyldimethyl, chlorides | Benzyl-C12-16-alkyldimethyl, chlorides | A | Rs | BO3150000 | 68424-85-1 |

TABLE 1-continued

| AOEC Exposure Code | Primary Name | Synonym | A = Asthmagen | RS = Asthma Sensitizer | Registry of Toxic Effects of Chemical Substances (RTECS) number | CAS number |
|---|---|---|---|---|---|---|
| 322.329 | Benzyl-C16-18-alkyldimethyl, chlorides | Benzyl-C16-18-alkyldimethyl, chlorides | A | Rs | BO3150000 | 68607-20-5 |

Quaternary amines are classified as asthmagens by the The Association of Occupational and Environmental Clinics. These data were found by searching http://www.aoec-data.org/ExpCodeLookup.aspx.

SUMMARY

One aspect of the present application relates to a method of manufacturing an absorbent non-leaching antimicrobial porous structure composite, comprising: mixing a solidifiable matrix in a flowable form such as a liquid or semi-liquid form with 1) a non-leaching and non-soluble, finely dispersed antimicrobial and 2) a removable pore-forming substance, wherein the pore-forming substance and the finely dispersed non-soluble non-leaching antimicrobial are evenly distributed and physically enveloped within the solidifiable matrix like raisins in raisin pudding; solidifying the solidifiable matrix into a solid matrix, wherein the solid matrix is solidified while physically enveloping the pore-forming substance and non-leaching antimicrobial; removing the pore-forming substance from the solid matrix by subjecting the solidified matrix to physical conditions that remove the solid pore-forming substance such as by melting or dissolution, wherein pores in the solid matrix are formed by the removal and thus absences of the pore-forming substance and wherein the pores in the pore-containing solid matrix have an average size of under 3 mm in width at their narrowest dimension; wherein the non-soluble non-leachable antimicrobial is now physically incorporated within the porous matrix composite and wherein in the non-leachable non-soluble antimicrobial represents ≤5% wt/wt of the dried, finished product; and removing any non-physically incorporated non-leachable antimicrobial from the pore-containing solid matrix for optional recovery and reuse. In this embodiment, the non-leaching porous antimicrobial composite is formed in one step.

In certain embodiments, the non-leachable antimicrobial porous composite is formed in two steps, physically incorporation of the non-leachable antimicrobial into the pore-containing solid matrix occurring after the solidification of the solidifiable matrix. Another aspect of the present application relates to a method of manufacturing of an absorbent non-leaching antimicrobial porous structure composite, comprising: mixing a solidifiable matrix in a flowable form such as a liquid or semi-liquid form with a removable pore-forming substance, wherein the pore-forming substance is evenly distributed and physically enveloped within the solidifiable matrix like raisins in raisin pudding; solidifying the solidifiable matrix into a solid matrix, wherein the solid matrix is solidified while physically enveloping the pore-forming substance and non-leaching antimicrobial; removing the pore-forming substance from the solid matrix by subjecting the solidifiable matrix to physical conditions that remove the solid pore-forming substance such as by melting or dissolution, wherein pores in the solid matrix are formed by the removal and thus absences of the pore-forming substance and wherein the pores in the pore-containing solid matrix have an average size of under 3 mm in width at their narrowest dimension; physically incorporating a non-leaching antimicrobial through deposition, such that the non-leaching antimicrobial is deposited in a more within all pores and irregularities of the now solid porous matrix, thus becoming physically bound and incorporated into the composite; wherein the now physically incorporated non-leachable represents ≤5% wt/wt of the dried, finished product; wherein the surface area to volume ratio of the deposited non-leachable antimicrobial exceeds 6,000:1 m$^{-1}$ and is most preferably in the range of 50,000-1,000,000 m$^{-1}$; and removing any non-physically bound, non-leachable antimicrobial from the pore-containing solid matrix for optional recovery and reuse. In this embodiment, the non-leaching porous antimicrobial composite is formed in two steps.

Another aspect of the present application relates to a method of manufacturing an absorbent non-leaching antimicrobial porous structure composite, comprising: mixing a solidifiable matrix in a flowable form such as a liquid or semi-liquid form with a removable pore-forming substance, wherein the pore-forming substance is evenly distributed and physically enveloped within the solidifiable matrix; solidifying the solidifiable matrix into a solid matrix, wherein the solid matrix is solidified while physically enveloping the pore-forming substance; removing the pore-forming substance from the solid matrix by subjecting the solidifiable matrix to physical conditions that remove the solid pore-forming substance such as by melting or dissolution, wherein pores in the solid matrix are formed by the removal and thus absences of the pore-forming substance and wherein the pores in the pore-containing solid matrix have an average size of under 3 mm in width at their narrowest dimension; physically incorporating a non-leaching non-soluble antimicrobial through physical chemical covalent attachment to the solid, porous matrix, such that the non-leaching antimicrobial is uniformly attached to the surface of the absorbent composite within its pores and irregularities; wherein the now physically bound antimicrobial is thus non-leachable and represents ≤2.5% wt/wt of the dried, finished product; wherein at least 50 molecules of non-leachable antimicrobial are anchored per cubic millimeter; and removing any non-physically bound antimicrobial from the pore-containing solid matrix for optional recovery and reuse. It is noted that depending on the chemistry of physical covalent attachment of the non-leaching antimicrobial, the physical incorporation may take place either after, during or before solidification.

In certain embodiments, the flowable solidifiable matrix typically in liquid or semi-liquid form comprises natural polymers such as cellulose, callose, laminarin, chrysolaminarin, xylan, arabinoxylan, mannan, fucoidan, arabinoxylan, galactomannan, galactomannan, arabinoxylans, inulin, amylopectin or pectins, non-natural polymers, thermosetting polymers, rubber (natural or artificial), and/or polymers based on acrylonitrile and styrenebutadiene. In the most preferred embodiments, the porous matrix is able to absorb from 1× its own weight in water to 50× its own weight in water. In further embodiments, the solid pore-forming substance comprises sodium sulfate, sugars (such as glucose, trehalose, fructose and many others), dissolvable or meltable natural polymers, dissolvable or meltable artificial polymers or salts comprising ammonium, calcium, magnesium, potassium, lithium, iron, aluminum and other metals and cations, pyridinium, quaternary, ammonium, sodium, acetate, silicate, carbonate, chloride, iodide, citrate, borate, benzoate, cyanide, fluoride and other halides, nitrate, nitrite, phosphate and/or sulfate and other anions as well as materials chosen for their specific solubility and/or melting point such as dimethylfulfoxide (DMSO) or other solvents, or lauric acid or other materials melting in the range of 0° C.-100° C. It is also recognized that a flowable solidifiable matrix which can be solidified at low temperature such as 0° C. makes possible the use of water ice as a pore-forming substance. In another preferred embodiment, the pores in the pore-containing solid matrix have an average minimum dimension of under 2 mm at their narrowest dimension. In another preferred embodiment, the pores in the pore-containing solid matrix have an average minimum dimension of under 1 mm at their narrowest dimension.

In particular embodiments, the non-leachable antimicrobial comprises copper, silver, zinc, bismuth, gold, aluminum, boron, selenium, gallium, sulfur, germanium, barium, manganese, vanadium, lead, beryllium, cadmium, chromium, arsenic, tellurium, mercury, thallium, uranium, tin, antimony, indium, iron, cobalt or nickel, strontium, scandium, titanium, manganese, yttrium, zirconium, niobium, molybdenum, technetium, ruthenium, rhodium, palladium, lanthanum, hafnium, tantalum, tungsten, rhenium, osmium, iridium, platinum, gold, mercury, actinium, rutherfordium, dubnium, seaborgium, bohrium, hassium, meitnerium, darmstadtium, roentgenium, copernicium, cerium, praseodymium, neodymium, promethium, samarium, europium, gadolinium, terbium, dysprosium, holmium, erbium, thulium, ytterbium, lutetium, thorium, protactinium, uranium, neptunium, plutonium, americium, curium, berkelium, californium, einsteinium, fermium, mendelevium, nobelium, or lawrencium in their pure form, compounded form or in chemical combinations.

Another aspect of the present application relates to a porous antimicrobial matrix composite, comprising: a composite of a flexible, absorbent, pore-containing matrix, said pores having the ability to absorb for example liquids, gases or some combination thereof, a non-leachable antimicrobial physically incorporated and thus composited within this matrix through physical anchoring and/or physical chemical covalent attachment; pores within the antimicrobial porous matrix composite, wherein the size of the pores is under 3 mm at their narrowest dimension, and wherein the pores retain the non-leachable antimicrobial within their interior, and further wherein the non-leachable antimicrobial physically incorporated into the porous matrix composite has a high surface-area to volume of the of at least $6,000{:}1\ m^{-1}$ and is most preferably in the range of $50{,}000\text{-}1{,}000{,}000\ m^{-1}$. In certain embodiments of the porous matrix insoluble antimicrobial composite, the non-leachable antimicrobial comprises copper, silver, zinc, bismuth, gold, aluminum, boron, selenium, gallium, sulfur, germanium, barium, manganese, vanadium, lead, beryllium, cadmium, chromium, arsenic, tellurium, mercury, thallium, tin, antimony, indium, iron, cobalt or nickel, strontium, scandium, titanium, yttrium, zirconium, niobium, molybdenum, technetium, ruthenium, rhodium, palladium, lanthanum, hafnium, tantalum, tungsten, rhenium, osmium, iridium, platinum, actinium, rutherfordium, dubnium, seaborgium, bohrium, hassium, meitnerium, darmstadtium, roentgenium, copernicium, cerium, praseodymium, neodymium, promethium, samarium, europium, gadolinium, terbium, dysprosium, holmium, erbium, thulium, ytterbium, lutetium, thorium, protactinium, uranium, neptunium, plutonium, americium, curium, berkelium, californium, einsteinium, fermium, mendelevium, nobelium, or lawrencium in their pure form, compounded form or in chemical combinations. In further embodiments, the surface of the antimicrobial matrix composite comprises nanopillars, wherein the nanopillars are arranged in an array pointed away from the surface of the composite. In other embodiments, the array of blunted spikes forms a hexagonal array.

Another aspect of the present application relates to a kit for maximizing the antimicrobial effects of the antimicrobial absorbent porous composite, the kit comprising: instructions (including for example information on proper use and storage); a cut piece of antimicrobial porous composite suitable for use as a cleaning, optionally and preferably affixed to a scrubber; and optionally a holder, wherein the holder contains the same or different antimicrobial as the antimicrobial porous composite. In certain embodiments, the antimicrobial porous composite and the holder employ a metal selected from the group comprising copper or silver or some combination of the two, or other non-leaching antimicrobial material or material composited or derivatized with antimicrobial. In certain embodiments, the holder is a container selected from the group comprising a space such as a bowl or a box, either enclosed or open, wherein the holder may be solid or porous (as formed by a screen or grate). The holder may be afforded a means to drain fluid.

BRIEF DESCRIPTION OF THE DRAWINGS

The above and other objects and advantages of the application will be apparent upon consideration of the following detailed description, taken in conjunction with the accompanying figures.

DETAILED DESCRIPTION

Figure 1:
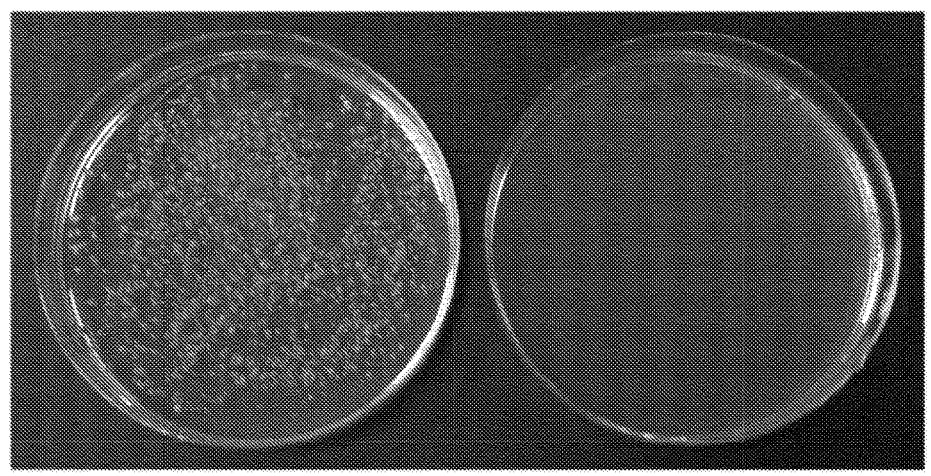
FIG. 1 shows cellulose porous matrix composites untreated (left) and treated (right), 0.1 ml plated on Petri dishes.

Some modes for carrying out the present invention are presented in terms of its exemplary embodiments, herein discussed below. However, the present invention is not limited to the described embodiment and a person skilled in the art will appreciate that many other embodiments of the present invention are possible without deviating from the basic concept of the present invention, and that any such work around will also fall under the scope of this application. It is envisioned that other styles and configurations of the present invention can be easily incorporated into the teachings of the present invention, and only one particular configuration shall be shown and described for purposes of clarity and disclosure and not by way of limitation of scope.

Headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

In the following, "antimicrobial" means a substance or agent that kills microorganisms, inhibits the growth, reproduction, attachment or colonization of a surface by microorganisms, or otherwise harms microorganisms.

Method of Manufacture of an Antimicrobial Porous Matrix Composite with Effective Pore Size In one aspect of the application, the manufacturing process can be broken down into six steps: 1) the creation of a flowable, formable, solidifiable matrix for example in liquid or semi-liquid form; 2) the provision to the matrix of pores of a specifically controllable size, optionally and preferably by incorporation into the formable matrix of a specifically removable substrate around which the matrix can solidify such as a dissolvable or meltable substance like a salt, wherein the pores are on or about 0.1-3 mm in diameter at their narrowest dimension, in some embodiments of an average size no greater than 3 mm across at their narrowest dimension, in a preferable embodiment in the range of an average size range ≤1-2 mm in at their narrowest measure; 3) the physical incorporation of a non-leachable antimicrobial, said physical incorporation being afforded either through physical anchoring (similar to the physical anchoring of raisins trapped in raisin pudding) or by physical chemical covalent attachment, during the solidification of the matrix while it contains the pore-forming substance or after its solidification, to provide a high surface-area to volume of the antimicrobial of at least $6,000:1\ m^{-1}$ and is most preferably in the range of $50,000-1,000,000\ m^{-1}$; 4) the solidification of the matrix around the pore-forming substrate; 5) the removal of the pore-forming substrate and 6) the removal, optionally and preferably for recovery and recycling, of any non-physically bound, non-leachable antimicrobial before distribution, sale or use. It is noted that the physical incorporation of antimicrobial may take place either before or after the solidification of the matrix, and that each order offers different advantages.

In certain embodiments, the solidifiable matrix is comprised of processed natural carbohydrate polymers such as cellulose. In some processed natural polymer embodiments, liquefaction of a carbohydrate matrix like cellulose may be achieved treating cellulose of an appropriate form (such as pulp) with sodium hydroxide (NaOH) to soften the cellulose by breaking the cellulose chains into smaller lengths (so called "aging"). This alkali cellulose is then treated with carbon disulfide ($CS_2$) to produce sodium cellulose xanthate, which, after removal of $CS_2$ by vacuum or other means, is dissolved in caustics to form viscose.

In other processed cellulose embodiments, liquefaction of the cellulose matrix from an appropriate source (such as wood chips or shredded cotton) is digested chemically to remove the lignin and soften for mechanically milling, optional bleached, dried and dissolved in a suitable solvent such as N-methylmorpholine N-oxide, dimethyl sulfoxide, dimethyl sulfoxide/lithium chloride, dimethyl sulfoxide/N-methylmorpholine N-oxide, and/or dimethylacetamide/lithium chloride to yield dope. In other processed cellulose embodiments, the cellulose matrix is liquefied with an alkaline aqueous processed containing copper sulfate in ammonia to make cuprammonium viscose. In further processed cellulose embodiments, cellulose is treated with an acylating reagent such as acetic anhydride or the like to produce cellulose acetate, which is then dissolved in a suitable solvent such as acetone.

In other embodiments of the invention, the matrix is a non-natural polymer, such as thermosetting polymers like phenol-formaldehyde, urea-formaldehyde, polyester, polyurethanes, vulcanized rubber, polyoxybenzylmethylenglycolanhydride (Bakelite), Duroplast, urea-formaldehyde, melamine or melamine-formaldehyde, diallyl-phthalate (DAP), epoxy resins, polyamide resins in combination with epoxy resins, polyimides, cyanate esters or polycyanurates, polyester resins, cellulose acetate-butyrate, ethyl cellulose, vinyl and vinylidene polymers and copolymers, polyvinyl alcohol containing thermosetting resins, acrylate and methacrylate resins, polystyrene, and others may be used, these polymers including optionally elastomeric materials such as rubber (natural or artificial), GRS (Government Rubber Styrene, a copolymer of butadiene and styrene), and/or various synthetic latices such as acrylonitrile and styrenebutadiene based polymers which can be made to be liquid or semiliquid and which may be incorporated in a mix of one or more polymers. One skilled in the art will recognize that multiple matrices are possible, and that depending on the matrix, the conversion from liquid or semiliquid into solid will employ changes in temperature (such as heating), pH (such as acidification), chemical reaction and the like.

The formable, solidifiable matrix, typically in a liquid or semi-liquid form, is then imparted with specifically removable materials around which pores can form. Control of pore size is essential to the efficaciousness of the end product as physically bound antimicrobial substances by definition are physically bound and are thus effective only over a given distance (for example through some distance of water). Although diffusion and Brownian motion will eventually bring microbes near or in contact with the microbial surface, where they will be ideally killed, the speed at which they are brought is made slower with larger pores. Likewise, the overall residence time (time of contact with the antimicrobial surface) is made shorter with large pores. Thus, control of pore size and specifically the prevention of the narrowest distance being too large are essential to the microbe killing effect of physically bound antimicrobials. While they can be symmetrical (round) or asymmetrical (needles) or other shapes, at their narrowest dimension, the pores should be on average no greater than 3 mm in diameter and in a preferable embodiment in the range of ≤1-2 mm in diameter. It is also emphasized that uniformity of pore size and, most specifically, the absence of very large pores is essential to antimicrobial effectiveness: one large pore could allow for a reservoir of harmful microbes as the large dimension would allow them to escape contact with the antimicrobial surface.

In one preferred embodiment, these pores are formed incorporating a specifically removable substrate into formable, solidifiable matrix typically in liquid or semi-liquid form. This pore-forming substance does not initially dissolve to a significant degree, allowing the pore-forming substance and solidifiable matrix to be evenly mixed, for example in a rotary screw- or drum-mixer, and be evenly incorporated into the matrix.

After the matrix is solidified, by example through changes in temperature or chemical reaction, the pore-forming substance is removed, for example by dissolution (e.g. washing out with water) and/or melting, thus leaving holes in the matrix where the pore-forming substance once was which exactly correlate to the size and shape of the formerly present solid pore-forming substance. It must be noted that the pore size of the resultant porous matrix is thus directly, precisely and easily controlled through the choice of size and shape of pore-forming substance: through processes such as simple sieving of the solid pore-forming substance, a minimum pore size can be selected and ensured.

It is noted that gases are easily removed and can also be used as the pore-forming substance. However, the control over pore size using solid, removable pore-forming substances is direct, much greater and much more reproducible. For example, gases may form non-uniform bubbles throughout the matrix (having, for example, smaller bubbles at the bottom where the pressure is greater, and larger bubbles at the top, where the pressure is less and where multiple bubbles may have coalesced into larger bubbles), gas bubbles can coalesce, forming larger pores, gases expand with temperature and, because of the sensitivity of gases to environmental conditions, the reproducibility of pore sizes produced through bubbling gases may be poor. Solid pore-forming substances do not compress and are not affected by changes in temperature until their melting points are reached. Importantly, even in the case that the particles of solid pore-forming substances come into close contact, it is likely that matrix material will still fall between them, maintaining the minimum pore size.

In some preferred embodiments, the pore-forming substance is in particular a salt such as sodium sulfate (Glauber's Salt). While sodium sulfate is preferable because of its low cost, toxicity, and ability to melt and be washed out, salts comprised of ammonium, calcium, magnesium, potassium, lithium, iron, aluminum and other metals, pyridinium, quaternary, ammonium, sodium, acetate, silicate, carbonate, chloride, iodide, citrate, borate, benzoate, cyanide, fluoride, nitrate, nitrite, phosphate, sulfate and other cations and anions are all usable depending on cost and availability, toxicity, solubility and melting point. One skilled in the art will recognize that a myriad of pore-forming materials may be employed so long as the pore-forming material maintains its shape and so long as pore-forming material(s) can be removed for example by dissolving, melting or the like. Materials are thus typically chosen for their specific solubility and/or melting point such as dimethylfulfoxide (DMSO) or lauric acid typically in the range of 0° C.-100° C. One skilled in the art also recognizes that a flowable solidifiable matrix which can be solidified at low temperature such as 0° C. makes possible the use of water ice as a pore-forming substance.

In other embodiments, the pore-forming substance is crystals of sugars such as glucose, trehalose, fructose, sucrose and many others. In other embodiments, the pore-forming substance is a meltable material such as natural polymers (including and not limited to carbohydrates like maltodextrins or agaroses, proteins like gelatin), lipids or artificial polymers which are either meltable, dissolvable, both meltable and dissolvable or otherwise removable (such as and not limited to poly(N-isopropylacrylamide) (PNIPAM) and polyacrylamide (PAM), poly(2-oxazoline) and polyethylenimine (PEI), poly(acrylic acid), polymethacrylate and other acrylic polymers, poly(ethylene glycol) and poly(ethylene oxide), poly(vinyl alcohol) (PVA) and copolymers, poly(vinylpyrrolidone) (PVP) and copolymers).

In all embodiments, properties are selected such that the pore-forming substance maintains a shape, most preferably by being solid, during conditions of incorporation into the flowable solidifiable matrix material, which is typically in liquid or semiliquid form, but is able to be melted, dissolved or otherwise removed after or during the process of solidification of the matrix material. Many embodiments of such materials are familiar to one skilled in the art. For example, especially polymer length and degree of crosslinking (if any) can modulate melting temperatures and solubilities. Certain substances alone, ideally chosen to be inexpensive, easily available and non-toxic, may exhibit the desired properties without modification. These examples are for illustrative purposes and not intended to limit embodiments of the present invention.

In one embodiment, at the time that the formable, typically liquid to semiliquid unsolidified matrix material is mixed with the pore-forming substance, insoluble antimicrobials such as and not limited to metallic copper, metallic silver or other insoluble or mostly insoluble, non-leachable antimicrobials or mix of antimicrobials is added during the rotary drum mixing step, allowing complete and easy integration into the manufacturing process without any changes. Powders (both regular spheres and irregularly shaped, these both solid and porous), shredded foils, stands and other geometries with high surface area to volume ratios of at least $6,000:1\ m^{-1}$ and is most preferably in the range of $50,000$-$1,000,000\ m^{-1}$ are preferred and mixed into the liquid or semiliquid matrix at the same time as the pore-forming substance such as salts. This mixing process allows the matrix to the matrix form physically encapsulating pockets around the non- or minimally-soluble antimicrobial: the antimicrobial is held as raisins in raisin pudding, a process further aided by the use of irregularly shaped insoluble antimicrobials. Surface area to volume ratios are calculated as the surface area divided by the volume. By example, the surface area to volume ratio of cubes of 1 cm (0.01 m) on each side would be $(6(0.01\ m)^2)/(0.01\ m)^3 = 600\ m^{-1}$. Ratios for other geometries are calculated based on their shapes. These examples are for illustrative purposes and not intended to limit embodiments of the present invention.

The antimicrobial-containing matrix is then extruded or formed into the desired geometry upon which time the matrix is solidified according to the properties of the matrix. In embodiments of processed cellulose such as in viscose form, this likely includes the application of heat and/or electrical current and/or washing in acidic conditions such as in a dilute solution of sulfuric acid. One skilled in the art will recognize the choice of matrix is not limiting on the scope of invention. Pore-forming substances are subsequently removed (by for example washing away and/or melting) and reclaimed. The resulting porous absorbent antimicrobial matrix composite is then thoroughly washed to remove, capture and reclaim any unbound insoluble antimicrobial. The thus washed product is then as needed and desired cut, dried, finished, and packaged. The product may be packaged with humectants like magnesium chloride, polyethylene glycol or surfactants or similar to maintain product softness and flexibility. Multiple non-soluble non-leaching antimicrobial materials including antimicrobial metals, antimicrobial compounds or mixtures thereof can be substituted alone or in combination for copper or silver. Copper represents a preferred embodiment due to its cost, availability, toxicity, efficacy and acceptability, followed by copper and silver. One skilled in the art will recognize the choice of non-soluble non-leaching antimicrobial materials is not limiting on the scope of invention. In this embodiment, the non-leachable non-soluble antimicrobial represents ≤5% wt/wt of the dried, finished porous matrix composite. By example, if 200 cm$^3$ of control porous matrix (which does not contain any non-soluble antimicrobial) weighed 95 g when washed and fully dried, 200 cm$^3$ of washed, fully dried antimicrobial porous matrix composite would weigh no more than 100 g, the additional 5 g (100−95 g=5 g) representing the weight of the non-soluble non-leaching antimicrobial and representing 5% by weight (5 g/100 g=5%).

In other embodiments of the invention, an insoluble or mostly insoluble antimicrobial is composited into the pores and surface irregularities of a ready matrix, for example after the pore-forming substance has been removed. This embodiment allows for the incorporation of antimicrobials onto preexisting matrices, for example into the pores of the cellulosic backbone of a natural *luffa* sponge from plants of the *Luffa* genus, and simultaneously generates an extremely high surface area to volume ratios of >6,000:1 m$^{-1}$ and often and is >50,000-1,000,000 m$^{-1}$ as the material is deposited typically in thin layers <1 mm thick, and finally, because the depositions are within the pores and exactly mirror the dimensions of the pores, presents an intrinsic mechanism of anchoring: the entrance to pores is typically smaller than the pore itself, and/or the pores have irregularities, thus physically trapping the deposited antimicrobial within the pores. In preferred embodiments, antimicrobial metals such as copper, silver or a mixture thereof are introduced. One skilled in the art will recognize the choice of non-soluble non-leaching antimicrobial materials is not limiting on the scope of invention so long as they can be added within the pores of preformed solid porous matrix.

In some preferred embodiments of the invention, the porous matrix is formed of materials from natural biological sources such as materials derived from plants, natural rubbers, celluloses, and/or marine animals of the phylum Porifera and/or Symplasma. In embodiments, suitable *luffa* gourds, also called "vegetable sponge" and/or "strainer vine" typically of the *Luffa* genus within the cucurbitaceae family, are employed. In other embodiments, sea sponges, including glass sponges (sometimes classified in the phylum Symplasma) also called hexactinellid sponges which have a skeleton made of four- and/or six-pointed siliceous spicules. Alternatively, in addition to processing natural polymers by the methods described herewithin, fibers from fiberous plants can be woven, for example coarsely woven, sewn or otherwise bound together to provide a multitude of porous matrices which provide for fluid and gas communication through a plurality of flow channels and pores in three dimensions. Such fibrous sources include and are not limited to coconut or hemp fibers, sea cucumber skeleton (*luffa*), and, vines, husks and fiber aggregates of plants such as rush grass, rice plant, *luffa*, buckwheat, soybean, bamboo, timber or sea grass etc. In addition, animal fibers such as hair, feathers, skin and hides, silk and wool may be employed in the same manner as plant fibers. Such materials are naturally available, are often waste products, are highly porous, inexpensive and fully biodegradable. One skilled in the art recognizes that plants represent a carbohydrate matrix, sea sponges and animal fibers a protein matrix, and glass sponges a silica matrix, all from natural sources. One skilled in art also appreciates that many natural species are potential sources of useful and useable matrix, and that these examples are in no way limiting.

In other embodiments of the invention, the non-leaching antimicrobial is incorporated into the porous antimicrobial matrix composite after the matrix has been solidified. In this embodiment, antimicrobials are physically covalently attached to the matrix, particularly including within its pores which are capable of absorbing solutions including microbes contained therewithin, in a manner consistent with the available functional chemical groups presented by the matrix and the antimicrobial. For example, NHS esters of antimicrobials can react with amino groups present in solidified flexible solid matrices. Amines, for example those of the backbone of amine-containing polymers like polyurathanes, can be likewise be reacted with halogenated forms of antimicrobials. Alternatively, halo-epoxyalkyl compounds such as a $C_1$-$C_6$ bromo-epoxyalkyl such as epibromohydrin can be reacted with the amines of the solidified matrix in the presence of a strong base such assodium hydride (NaH) or lithium diisopropylamide (LDA), allowing installation of a reactive epoxy ring and subsequent reaction with other functional groups such as those of antimicrobials. It is recognized by one skilled in the art that this theme of addition of the installation of or conversion to a more convenient reactive functional is equally applicable to other functional groups outside of amines and is well developed in chemical literature. Likewise, activated esters such as acid chlorides, R(CH2)COCl or anhydrides (R(CH2)O)2O where R is an antimicrobial or mixture thereof can be reacted with the nucleophilic groups such as hydroxyls or amines. Derivatized silanes of the formula RSiX1X2X3 where R are antimicrobials can be reacted with silica containing substrates such as sea sponges. It is further noted that silane derivatization agents like GPTMS ((3-glycidyloxypropyl) trimethoxysilane) which bear reactive moieties such as epoxides allow installation of a reactive epoxide and further reaction with other functional groups. Acid anhydrides of the form RCOOCOR where R is an antimicrobial can react with hydroxyls. Hydroxyls of the underlying formed flexible porous matrix can also be reacted with antimicrobials containing a hydroxyl by esterification. Hydrazines of the form NH2NH—R where R is an antimicrobial can be reacted with carbonyls. The methods of manufacture used in various embodiments is not limiting and may include incorporation within the composite with deposition solutions or chemical surface derivatization. It is emphasized that the non-soluble antimicrobial, or antimicrobial made non-soluble by physical covalent attachment within the composite, by necessity must present its surface to the porous areas of the composite capable of absorbing. It is also emphasized and known to one skilled in the art that a huge number of chemistries can be used to effect covalent bonds including coupling with AOP, BOP, Brop, Carbodiimide, COMU, Cyano-hydroxyimino-acetic acid ethyl ester (Oxyma), DCC, DPPA, EDAC, EDC, EDCI, EEDQ, HATU, HDMC, HOSu, phosphorous oxychloride, PyAOP, PyBOP, PyOxim, TATU, TBTU, TFFH, thionyl chloride, TOTT and many other reagents and chemistries known to one skilled in the art.

It is recognized that in uses of cleaning, utility is maximized by the inclusion of an abrasive surface or scrubber, which must be rough and which preferably also contains, is made of or composited with an insoluble antimicrobial. The antimicrobial activity may also be applied through antimicrobial incorporation or deposition to other objects subject to microbial contamination such as brushes of various sizes (tooth- or toilet-brushes), surfaces such as shelves, tables and countertops of composites, ceramic or glass, containers such as the food drawers of refrigerators or lunch bags or plastic bags, and other commonly contaminated areas such as the seals around refrigerator- or dishwasher doors. In these embodiments it is recognized that many methods of manufacture can be applied to generate the necessary elements of sufficient insoluble antimicrobial, this insoluble antimicrobial being firstly accessible to air and this insoluble antimicrobial secondly being widely distributed throughout the object and having large surface area of at least 6,000:1 $m^{-1}$ and is most preferably in the range of 50,000-1,000,000 $m^{-1}$, and a matrix material which holds the insoluble antimicrobial, this matrix material holding the insoluble antimicrobial physically or covalently or both. Given sufficient insoluble antimicrobial and distribution these embodiments exhibit the anti-bacterial properties of the porous flexible absorbent antimicrobial composite herein.

Multiple insoluble antimicrobials such as copper, silver and multiple other metals as well as other insoluble materials such as sulfur exhibit microbe killing effects and can be similarly composited by physical incorporation or deposition into the porous matrix. A antimicrobial deposition solution is made but with silver in place of copper. Multiple metals can be combined in the same or subsequent depositions. Powders of insoluble antimicrobials such as copper or silver—pure, in mixtures or in chemical combinations—can also be incorporated. Chelators and/or ion exchange surfaces or matrices and/or zeolites or other porous or holding structures that can accommodate metal ions or other antimicrobials can also be added, e.g., cyclodextrins can be used to hold organic antimicrobials in the structure.

Other metals and elements that might be incorporated (as well as their mixtures and compounds) include most preferably copper, silver, zinc, bismuth, aluminum, boron, selenium, gallium, sulfur, germanium, barium or vanadium. Situation depending, the antimicrobial composition may include lead, beryllium, cadmium, chromium, arsenic, tellurium, mercury, thallium, uranium, tin, antimony, indium, iron, cobalt or nickel. The antimicrobial composition may also contain strontium, scandium, titanium, manganese, yttrium, zirconium, niobium, molybdenum, technetium, ruthenium, rhodium, palladium, lanthanum, hafnium, tantalum, tungsten, rhenium, osmium, iridium, platinum, gold, mercury, actinium, rutherfordium, dubnium, seaborgium, bohrium, hassium, meitnerium, darmstadtium, roentgenium, copernicium, cerium, praseodymium, neodymium, promethium, samarium, europium, gadolinium, terbium, dysprosium, holmium, erbium, thulium, ytterbium, lutetium, thorium, protactinium, neptunium, plutonium, americium, curium, berkelium, californium, einsteinium, fermium, mendelevium, nobelium, or lawrencium as pure elements, as compounds, as mixtures or in chemical combinations. Compounds may include covalent compounds or salts such as halide slats.

In addition to elements, their compounds, salts, mixtures and chemical combinations, the antimicrobial incorporated preferably through physical chemical covalent attachment, though also though incorporation of e.g. an insoluble high surface area to volume polymer of antimicrobial may include alkylated Polethylenimines including long-chained hydrophobic cations poly(vinyl-Nhexylpyridinium)(PVP) where chains ranges especially of 3-8 PVP chains per unit are efficient or similarly N-hexylated+methylated high molecular-weight polyethylenimine (PEI). Alternative forms of alkyl chains with cationic portions include compounds of 1,4-diazabicyclo[2.2.2]octane (DABCO) covalently attached to different carbohydrate-based surfaces. Antimicrobials may also include Quaternary ammonium compounds in particular Quaternary Silanes (Si-QAC) e.g. 3-(trihydroxysilyl) propyldimethyl-octadecyl ammonium chloride, Zinc Pyrithione, Polyhexamethylene Biguanide or Triclosan. Additionally, the antimicrobial incorporated may include ceragenins, or cationic steroid antimicrobials (CSAs), phenoxyethanol, triclosan, 7-ethylbicycleoxazolidine, benzoic acid, bronopol, butylparaben, chlorphenesin, diazolidinyl urea, dichlorobenzyl alcohol, dimethyl oxazolidine, DMDM hydantoin, ethylparaben, hexamidine diisethionate, imidiazolidinyl urea, imidiazolidinyl urea NF, iodopropynyl butylcarbamate, isobutylparaben, methylparaben, potassium sorbate NF FCC, propylparaben, quaternium-15, sodium benzoate NF FCC, sodium caprylate, sodium dehydroacetate, sodium dehydroacetate FCC, sodium hydroymethylglycinate, sodium hydroxymethylglycinate, sodium methylparaben, sodium propylparaben, sorbic acid NF FCC, anisic acid, benzethonium chloride, caprylic/capric glycerides, caprylyl glycol, di-alpha-tocopherol, ethylhexylglycerin, glyceryl caprate, lysostaphin and/or lysozyme or similar, methyl isothiazolinone, polymethoxy bicyclic oxazolidine. Tocopheryl acetate, alcohol, benzalkonium chloride, benzethonium chloride, *camellia sinensis* leaf extract, *Candida bombicola*/glucose/methyl rapeseedate, hydrogen peroxide, methylbenzethonium chloride phenol, *pinus pinaster* bark extract, Poloxamer 188, PVP-Iodine, *Rosmarinus officinalis* Leaf extract, *Vitis vinifera* seed extract, ammomium benzoate, ammonium propioante, 5-Bromo-5-nitro-1,3-dioxane, Chloroxylenol, anti-microbial polycationic dendrimers especially but not limited to G3KL (sequence $(KL)_8(KKL)_4(KKL)_2KKL$) and G3RL (sequence $(RL)_8(KRL)_4(KRL)_2KRL$) and their dendrimers, lysine with its ε-amino and carboxyl groups free, Ethyl alcohol, Glutaral, Iodopropynyl butylcarabamate, Isothiazolinone, Parabens, Piroctone olamine, Selenium disulphine, Sorbic acid (mold), Zinc pyrithione, Benzalkonium chloride, Benzethonium chloride, Benzoic acid, Dehydroacetic acid, Dimethyl hydroxmethyl pyrazole, Formaldehyde, Hexetidine, Mthyldibromo glutaronitrile, Salicylic acid, Sodium hydroxymethylglycinate, Sodium iodate, Zinc oxide, Benzyl alcohol (mould), Boric acid (yeast), Chloroacetamide, Phenoxythanol, Ortholphenylphenol, Benzalkonium chloride, Benzethonium chloride, 5-Bromo-5-nitro-1,3-dioxane, Bronopol, Diazolidinyl urea, Dimethyl hydroxmethyl pyrazole, Dimethyl oxazolidine, DMDM hydantoin, Ethyl alcohol, 7-Ethyl bicycloxazolidine, Formaldehyde, Glutaral, Imidazolidinyl urea, Isothiazolinone, Methenammonium chloride, Methylbromo glutaronitrile, Parabens, Polymethoxy bicylooxazolidine, Quaternium-15, Sodium hydroxymethylglycinate, Thimersal, Benzoic acid, Benzyl alcohol, Chlorhexidine, Hexetidine, Phenethyl alcohol, Polyaminopropyl biguanide, Polyquarternium-42, Salicylic acid, Sodium iodate, Triclocarban, Triclosan, Zinc phenol sulphonate, Chloroacetamide, Chlorobutanol, Dehydroacetic acid, Neem seed oil, Parabens, Phenoxyethanol, Tee trea oil, Usnic acid, Ammonim Benzoate, Ammonium Propionate, Benziosthiazolinone, Benzoic Acid, Benzotriazole, Benzyl Alcohol, Benzylhemiformal, Benylparaben, 5-Bromo-5-Nitro-1,3-Dioxane, 2-Bromo-2-Notropropane-1,3-Diol, Butyl Benzoate, Butylparaben, Calcium Benzoate, Calcium Paraben, Calcium Propionate, Calcium Salicylate, Calcium Sorbate, Captan, Chloramine T, Chlorhexidine Diacetate, Chlorhexidine Digluconate, Chlorhexidine, Dithydrochloride, Chloroacetamine, Chlorobutanol, p-Chloro-m-Cresol, Chlorophene, p-Chlorophenol, Chlorothymol, Chloroxylenol, *Citrus Grandis* (Grapefruit) Fruit Extract, *Citrus Grandis* (Grapefruit) Seed Extract, Copper Usnate, m-Cresol, o-Cresol, p-Cresol, DEDM Hydantoin, DEDM Hydantoin Dilaurate, Dehydroacetic Acid, Diazolidinyl Urea, Dibromopropamidine Diisethionate, Dimethyl Hydroxymethyl Pyrazole, Dimethylol Ethylene Thiourea, Dimethyl Oxazolidine, Dithiomethylbenzamide, DMDM Hydantoin, DMHF, Domiphen Bromide, Ethyl Ferulate, Ethylparaben, Ferulic Acid, Formaldehyde, Glutaral, Glycerol Formal, Glyoxal, Hexamidine, Hexamidine Diparaben, Hexamidine Paraben, 4-Hydroxybenzoic Acid, Hydroxymethyl Dioxazabicyclooctane, Imidazolidinyl Urea, Iodopropynyl Butylcarbamate, Isobutylparaben, Isodecylparaben, Isopropyl Cresols, Isopropylparaben, isopropyl Sorbate, Magnesium Benzoate, Magnesium Propionate, Magnesium Salicylate, MDM Hydantoin, MEA-Benzoate, MEA o-Phenylphenate, MEA-Salicylate, Methylchloroisthiazolinone, Methyldibromo Glutaronitrile, Methylisothazolinone, Methylparaben, Mixed Cresols, Nisin, PEG-5 DEDM Hydantoin, PEG-15 DEDM Hydantoin, PEG-5 Hydantoin Oleate, PEG-15 DEDM Hydantoin Stearate, Phenethyl Alcohol, Phenol, Phenoxyethanol, Phenoxyethylparaben, Phenoxyisopropanol, Phenyl Benzoate, Phenyl Mercuric Acetate, Phenyl Mercuric Benzoate, Phenyl Mercuric Borate, Phenyl Mercuric Bromide, Phenyl Mercuric Chloride, Phenylparaben, o-Phenylphenol, Polyaminopropyl Biguanide, Polyaminopropyl Biguanide Stearate, Polymethoxy Bicyclic Oxazolidine, Polyquaternium-42; Potassium Benzoate, Potassium Ethylparaben, Potassium Methylparaben, Potassium Paraben, Potassium Phenoxide, Potassium o-Phenylphenate, Potassium Propionate, Potassium Propylparaben, Potassium Salicylate, Potassium Sorbate, Propionic Acid, Propyl Benzoate, Propylparaben, Quaternium-8, Quatemium-14, Quaternium-15, Silver Borosilicate, Silver Magnesium Aluminium Phosphate, Sodium Benzoate, Sodium Butylparaben, Sodium p-Chloro-m-Cresol, Sodium Dehydroacetate, Sodium Ethylparaben, Sodium Formate, Sodium Hydroxymethane Sulfonate, Sodium Hydroxymethylglycinate, Sodium Isobutylparaben, Sodium Methylparaben, Sodium Paraben, Sodium Phenolsulfonate, Sodium Phenoxide, Sodium o-Phenylphenate, Sodium Propionate, Sodium Propylparaben, Sodium Pyrithione, Sodium Salicylate, Sodium Sorbate, Sorbic Acid, TEA-Sorbate, Thimerosal, Triclocarban, Triclosan, Undecylenoyl PEG-5 Paraben, Zinc Pyrithione or combinations thereof, such as for example Benzyl alcohol/mehtylchloroisothiazolinone/methylisothiazolinone, Benzyl alcohol/PPG-2 methyl ether/bronopol/deceth-8/iodopropynyl/butylcarbamate, Chloroacetamide sodium benzoate, Dehydroacetic acid/benzyl alcohol, Diazolidinyl urea/iodopropynyl butylcarbamate, Diazolidinyl urea/methylparaben/ethylparaben/butylparaben/propylparaben/isobutylpara ben/2-phenoxyethanol, DMDM hydantoin/iodopropynyl butylcarbamate, Glycerin/water/ethoxdiglycol/caprylyl glycol/sodium polyacrylate, Glyceryl laurate/caprylyl/phenylpropanol/dipropyleneglycol, Isopropylparaben/isobutylparaben/butylparaben, Methyl chloroisothiazolinone/methyl isothiazolinone, Methyldibromo glutaronitrile/methylchloroisothiazolinone/methylisothiazolinone/phenoxyeth anol, Methyldibromo glutaronitrile/phenoxyethanol, Methylchloroisothiazolinone/methylisothiazolinone, Methylparaben/ethylparaben/butylparaben/propylparaben/butylenesglycol, Methylparaben/ethylparaben/butylparaben/propylparaben/isobutylparaben, Methylparaben/ethylparaben/butylparaben/propylparaben/isobutylparaben/2-phenoxy-ethanol/bronopol, Methylparaben/ethylparaben/butylparaben/propylparaben/1,3-butylene glycol isomer, Methylparaben/propylparaben, Methylparaben/propylparaben/benzyl alcohol, Methylparaben/propylparaben/bronopol/phenoxyethanol, Methylparaben/propylparaben/bronopol/propylene glycol, Methylparaben/propylparaben/ethylparaben, Methylparaben/propylparaben/propylene glycol/diazolidinyl urea, Phenoxyethanol/benzoic acid/dehydroaceticacid, Phenoxyethanol/benzyl alcohol/potassium sorbate/tocopherol, Phenoxylethanol/chlorphenesin/glycerin/methylparaben/benzoic acid, Phenoxyethanol/DMDMhydantoin/Iodopropynyl butyl carbamate, Phenoxyethanol/DMDM hydantoin/methylparaben/propylparaben, Phenoxyethanol/isopropylparaben/isobutylparaben/butylparaben, Phenoxyethanol/methyldibromo glutaronitrile/idopropynyl butylcarbamate, Phenoxyethanol/methylparaben/butylparaben/ethylparaben/propylparaben, Phenoxyethanol/methylparaben/butylparaben/ethylparaben/propylparaben/isobutylparaben, Phenoxyethanol/methylparaben/isobutylparaben/butylparaben, Phenoxythanol/triethylene glycol/dichlorobenzylalcohol, Polyaminopropyl biguanide/parabens/phenoxyethanol, PPG-2 methyl ether/sodium benzoate/potassium sorbate/iodopropynyl butylcarbamate, Propylene glycol/benzyl alcohol/methylchloroisothiazolinone/methylisothaizolinone, Propylene glycol/diazolidinylurea/iodopropynyl butylcarbamate, Propylene glycol/diazolidinyl urea/methylparaben/propylparaben, Propylene glycol/MDMD hydantoin/methylparaben, Propyleneglycol/MDMD hydantoin/methylparaben/propylparaben, Propylene glycol/lichen extract, Propylene glycol/phenoxyethanol/chlorphenesin/methylparaben, Sodium levulinate/phenylpropanol combinations or similar.

In all cases, compounds may be pure, derivatives, mixtures, salts or mixtures thereof, and they various compounds may be mixed. Alternatively, various natural antibacterial agents such as antibiotics may be immobilized on surfaces, for example by incorporation into an ethylene-vinyl alcohol copolymer (EVOH). In all cases, the antimicrobial is composited either through physical anchoring (as raisins in raisin pudding) or physical chemically by covalent attachment. In certain embodiments, radioactive derivatives or nucleotides of the compounds listed herein may be used.

A Cicada Wing Nanostructured Surface Porous Antimicrobial Matrix

The antimicrobial effect of any or all of the antimicrobials herein, or antimicrobials plus the underlying substrate, may be increased by physical shape. For example, "The danger cicada (*Psaltoda claripennis*) is a locust-like insect whose wings are covered by a vast hexagonal array of 'nanopillars'—blunted spikes on a similar size scale to bacteria. When a bacterium settles on the wing surface, its cellular membrane sticks to the surface of the nanopillars and stretches into the crevices between them, where it experiences the most strain. If the membrane is soft enough, it ruptures." (Antibacterial 'nanopillars' on cicada wings pull bacterial membranes apart. Trevor Quirk. 4 March. Nature. doi:10.1038/nature.2013). Thus, any of the above may be formed in a physical shape, for example (and not limited to) in biomimicry of the cicada wing, such that it assists in antimicrobial activity. Multiple techniques may be used to create microorganism-disrupting nanoshapes, ideally spaced at an average distance of about 0.5 to about 200 micrometers apart, including plasma etching (based on reactive-ion etching), acid-mediated etching, anodic oxidation (including of metallic surfaces such as those presented by metallic insoluble antimicrobials), controlled polymer coatings photolithography, nanoimprint lithography, colloidal and E-beam lithography, μ-contact printing, dip-pen nanolithographya and hydrothermal etching (see Bhadra, C. M., Truong, V. K., Pham, V. T., Al Kobaisi, M., Seniutinas, G., Wang, J. Y., Juodkazis, S., Crawford, R. J. and Ivanova, E. P., 2015. Antibacterial titanium nano-patterned arrays inspired by dragonfly wings. *Scientific Reports,* 5) as well as other chemical means.

It is apparent to one skilled in the art that biomimic surfaces of cicada wing nanostructures may be physically incorporated into the composite during the solidification step of the flowable matrix (by example by adding insoluble antimicrobials bearing a surface structure of nanopillars) or after physical deposition of the insoluble antimicrobial into the solidified porous composite. In the later case, chemical processes in particular may be used to generate the requisite surface of nanopillars such as etching or deposition processes.

A Kit for Maximizing the Antimicrobial Action of the Porous Absorbent Antimicrobial Composite In certain embodiments, a kit for maximizing the antimicrobial effects of the antimicrobial porous composite, may comprise: instructions on proper use and storage; a cut piece of antimicrobial porous composite suitable for use as a cleaning, optionally and preferably affixed to a scrubber; and optionally a holder, wherein the holder contains the same or different antimicrobial as the antimicrobial porous composite. The holder is a container, such as a bowl or a box, into which the porous matrix composite is placed which: 1) allows the porous matrix to drain either through grating, holes, slots or screens; 2) is designed to be dishwasher safe; and 3) in the preferred embodiment, the holder contains, is made of, covered in or composited with copper, silver or another non-soluble antimicrobial material. Such a kit maximizes the antimicrobial action of the porous antimicrobial composite. The holder is designed so that when resting within the holder, the material of the porous matrix composite is in direct physical contact with the antimicrobial surface of the holder. One skilled in the art recognizes that the holder may be made of many suitable materials such as metal or plastic, so long as the material is intrinsically antimicrobial or allows for compositing or coating in a non-soluble antimicrobial material.

Other Modes of Use

In addition to the use of household and other items, the use of physically or covalently anchored antimicrobials maybe used in other functions outside of e.g. sponges or mops. This might include, for example, applications in water treatment (drinking water, wastewater, cooling water and so forth), applications in air treatment or filtration (for example in ventilation) and applications in water or food storage. In the cases of treatment of a gas or fluid, a porous matrix type physical embodiment is appropriate. Alternatively, a series of channels or tubes, a honeycomb, a column of beads such as in liquid chromatography or for that matter any other geometric arrangement which results in a high surface area to volume is preferred. In the case of storage, the storage container may simply be treated on the surface that contacts the substance for which microbes are undesirable e.g. food or water. Alternatively, the storage container walls or areas thereof may be fashioned to increase surface area.

It is recognized that the principle of incorporation either chemically or physically (raisin pudding) of antimicrobials reduces non-leaching thereby mitigating exposure of people, animals and the environment. Thus, this invention is useful for anti-fouling and antimicrobial paints for inside and outside use, antimicrobial wallpapers, antimicrobial dressings and plasters, prostheses and bone cement with antimicrobial activity, dental fillings, dental prostheses, antimicrobial cat litter, antimicrobial diapers, tampons or sanitary towels, ambient fragrances for rooms or cars, absorbent pads, air conditioning (filters and ducts), air inflated construction (air halls), agricultural and mulch films, all purpose adhesives, appliances and equipment, appliance adhesives and sealants, aprons, artificial leather, artificial plants, artificial wood, and plastic lumber, astroturf, automobile parts, automotive and truck upholstery, awnings, bags, bandages, barrier fabrics, bathroom accessories, bathtubs, bedding, beverage dispensers, bibs, boats, boat covers, book covers, bottles, brush bristles, brush handles, brooms, building components (walls, wallboard, floors, concrete, siding, roofing, shingles, hardware, carpet cleaner, ceilings and commercial and industrial applications), cable sheathing, caps (hats), cardboard, carpet and carpet underlay, caster wheels, cat litter, clinical thermometers, coats, compact discs, convertible tops, cookware, coolers, cooling towers, counter and table tops, conveyor belts, countertops, credit cards, crates (food and non-food), cups, currency, curtains, cushion pads, cutting boards, decking, dishes, dish cloths, dishwasher components, diving equipment or snorkels, drainage sewer pipe, draperies, exercise equipment, equipment for slaughterhouses or creameries or diaries, equipment for gyms, saunas or massages, fan blades, fibrefill, filters, fittings, fences, floor coverings, floor and carpet baking, flooring, foam (cushion, mattress), food preparation appliances, food and beverage processing equipment, food and drink containers, storage and bags, food handling equipment, food packaging, food and meat crates, food trays and covers, food wrap, footwear (including boots, sports equipment, and tools), fruit and vegetable brushes, fruit crates, furniture, garbage bags, garbage cans, garment bags, gaskets, general purpose containers, gloves, gowns (medical and consumers), grease traps, rigid greenhouses, greenhouse films, grout and joint compound, heating, ventilation and air conditioning, hoses, ice-making equipment and trays, incontinence care products, indoor and outdoor furniture, industrial equipment, inflatable bed, insulation for wire and cable, insulators, intimate apparel, jacket liners, janitorial equipment, kitchen and bathroom hardware, kitchen sinks and fixtures, kitchen towels, laminate and tile adhesives, laying batteries, life vests, liners, mats, mattress cover pads and filing, mattress adhesives, medical and dental apparel, mobile homes, mobile toilets, mops, money, natural and synthetic fibres and fabrics, non-woven fabrics, outerwear, packaging, pallets, paper products (wipes, tissues, wall coverings, towels, book covers, mulch), pillow covers, pipes, pipe sealant and insulating materials, plaster, plastic films, plates and utensils, playground equipment, plumbing supplies and fixtures (including toilet bowl seats), plumbing adhesives and sealants, pool liners, process vessels, protective covers, refrigerator components, roofing sheets, membranes, shingles and flashing, ropes, rugs, sales counter, sails, sanitary pipes, sealing compounds for bathrooms, kitchens or glass, sheets and blankets, shoes, shoe insoles, shower curtains, shower tubs, siding for housing, silage wrap, silos, sinks, siphons, skylights, sleeping bags, sleepwear, socks and hosiery, sponges, sprinkler, sportswear and sports equipment, storage containers, stucco, sun roof, sun shades, napkins, tanks, tape, tarps, telephone boxes or public phones, tents and other outdoor equipment, ticking (mattress pillow), tiles, tile grout, toothbrush handle and bristles, toilet paper and handkerchiefs, toilet blocks and cleaners, towels, toothbrush tumbler, toys, trim for outerwear and garments, trunk liners, tubing, umbrellas, undergarments, uniforms, upholstery, vacuum cleaner bags, wall and floor covering, wallpaper, waste bags, water tanks, waste containers, water treatment, water and ice handling equipment and filters, wet suits, wipes, wire and cable, wood and wood filled plastics. In all applications, it is possible to make the underlying base from many different materials, as long as that material supports the anchoring via chemical or physical means of the antimicrobial element, compound or mixture thereof.

The following examples are for purposes of illustrating certain embodiments of the application and are not limiting in any way.

EXAMPLES

Materials and Methods

Commercial preformed cellulose matrices were washed with commercial laundry detergent and very hot water for 10 complete cycles in a commercial cloths washer on its longest setting to remove their antibacterial compounds as well as glycerol, PEG and magnesium chloride used to keep sponges flexible. When dried, the sponges were hard, indicating such compounds had been removed. In all experiments, a washed but non-composited sponge served as the control. In all experiments, bacterial loads were assessed by plating and incubation on LB agar plates (10 g Bactotryptone, 5 g yeast extract, 10 g NaCl, 15 g agar, pHed to 7.5 and brought to 1 L; solution was sterilized by autoclaving for 1 hr in a commercial pressure cooker at ~20 psi) poured into 100 mm by 15 mm petri dishes. Fresh or recrystallized ascorbic acid should be used.

Example 1

Cleaned commercially available cellulose matrices were placed in a Ziploc bag for post-solidification incorporation of an insoluble antimicrobial, in this case copper. Per matrix, 50 ml of a solution of 10 mM copper sulfate, 20 mM acetic acid and 20 mM ascorbic acid was added. Except for copper sulfate, which is used to control pathogens in fish by adding it to the water, the reagents are non-toxic and suitable for food. Air bubbles were removed by repeated compression and release of the cellulose matrix and the cellulose matrix saturated with the copper incorporation solution was kept warm around 35-40° C. overnight. Copper incorporation was noticeable the next day on the cellulose matrix (both on and within the cellulose matrix and on the scrubbing surface, which became noticeably darker). Cellulose matrices now composited with insoluble antimicrobial were washed for a full cycle in a clothes washer as described for the preparation of the matrices prior to compositing to remove all non-physically bound antimicrobial (here copper) from the porous composite. The cellulose porous composite developed a very slight bluish tint over time, a color indicative of the presence of copper and it becoming oxidized in air.

To test for antibacterial activity, an untreated commercially available cellulose matrix (of the same brand) was left in the bottom of a sink for over a month and not sterilized. It remained moist, allowing bacteria to grow. Bacterial juice containing all microorganisms and other material removable from the porous cellulose was squeezed out and larger particles such as food chunks (but not bacteria) were removed by filtration through paper towels. The bacteria juice appeared translucent and had the distinct and unpleasant smell of rotten sponges. The bacteria juice was diluted 1:20 with tap water and 40 ml of diluted sponge juice was applied to both a flexible porous cellulose antimicrobial composite and a washed e porous cellulose matrix not containing the insoluble antimicrobial (copper) as a control.

The cellulose matrix was placed in a Ziploc bag to prevent evaporation, left for 8 hrs in a warm environment (30-40° C.) to facilitate bacterial growth. These matrices were squeezed out, any large particles were removed as described above. 0.5 mL of this solution was plated on LB plates and allowed to grow overnight. The plate from the flexible porous cellulose antimicrobial composite had zero colonies. In contrast, the plate from the control had an uncountable lawn of bacteria growth, indicating a many-log reduction in bacteria load (see Table 2).

TABLE 2

| Untreated (CFU) | Treated (CFU) |
| --- | --- |
| Uncountable lawn | 0 |

Example 2

Further experiments performed insoluble antimicrobial incorporation in plastic bottles rotated on a commercial rock tumbler. A natural *luffa* matrix, commercial cellulose matrix, sea sponge matrix and a polyurethane matrix were placed in the plastic bottle and one liter of the antimicrobial incorporation solution prepared in the same manner was poured onto them. Bubbles were removed by compression and expansion of the porous matrix materials using a plastic rod and the matrices were allowed to incorporate insoluble antimicrobial overnight as in Example 1 but with the rock tumbler rotating the matrices and antimicrobial deposition solution.

The next day, copper incorporation into the matrix/antimicrobial composite was noticeable on and in the matrices as in Example 1. Because the sea sponge was very close in color to the color of copper, it was not possible to visually determine if copper incorporation occurred within it. All matrices were washed for one cycle. Deposits on the polyurethane matrix appeared to have been washed away, indicating the necessity of incorporation during the solidification of the matrix. The *luffa* and cellulose matrices turned bluish with time, as in Example 1.

Testing for bacterial growth was performed as in Example 1 with the following modifications: first, bacteria juice was diluted 1:1000 to reduce the number of plated bacteria and allow for colony-forming-unit (CFU) counting. Second, due to the varying size of matrices, all composites were immersed in diluted bacteria juice and allowed to drip on a grate until no drops fell. It should be noted that while the exact same bacteria-containing juice was used for experiment and control, the initial number of bacteria per ml varied as a function of different kitchen activities (see Table 3).

TABLE 3

| Sponge type | Untreated (CFU) | Treated (CFU) |
| --- | --- | --- |
| Cellulose | 5314 | 0 |
| Luffa | 3121 | 0 |

The test was repeated for cellulose antimicrobial matrix composites with incubation at room temperature rather than 30-40° C. (see Table 4).

TABLE 4

| Untreated (CFU) | Treated (CFU) |
| --- | --- |
| 2719 | 2 |

The test was repeated with the exception that the concentration of the reagents for the copper incorporation reaction were doubled to 20 mM copper sulfate, 40 mM acetic acid and 40 mM ascorbic acid. As expected, additional copper incorporation was noticed. It was also observed that at those locations where the porous matrix contacts the side of the plastic bottle, deposits were enriched. Such deposits probably occur on the sides of the plastic bottle and are incorporated into the composite. They were not removed in one cycle with a clothes washer and remained on the composite during use in cleaning and absorption (see Table 5).

TABLE 5

| Untreated (CFU) | Treated (CFU) |
|---|---|
| >10,000 (estimated) | 0 |

Figure 2:
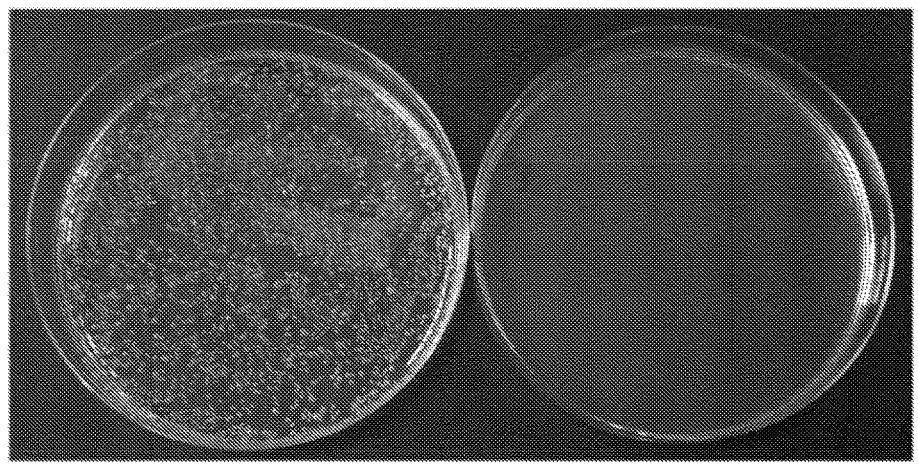
FIG. 2 shows cellulose porous matrix composite untreated (left) and treated (right), 0.5 ml plated plated on Petri dishes.
Figure 3:
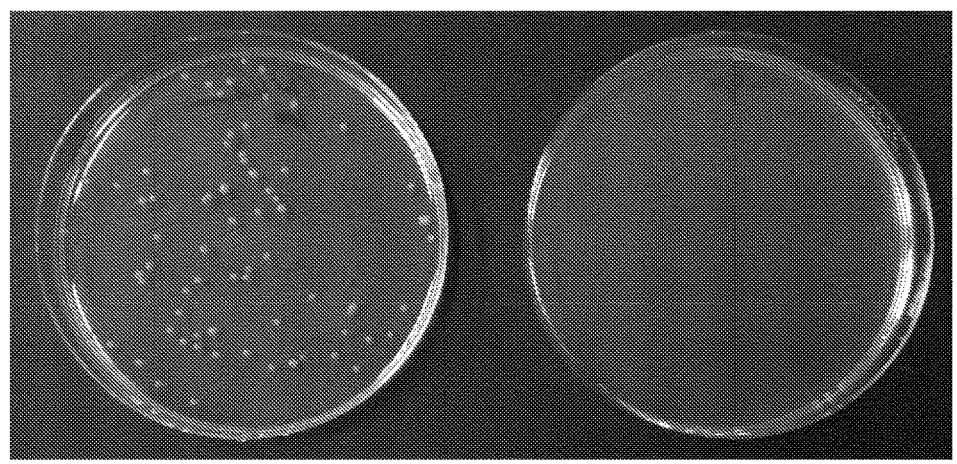
FIG. 3 shows antimicrobial cellulose untreated (left) and treated (right), 0.1 ml plated plated on Petri dishes.
Figure 4:
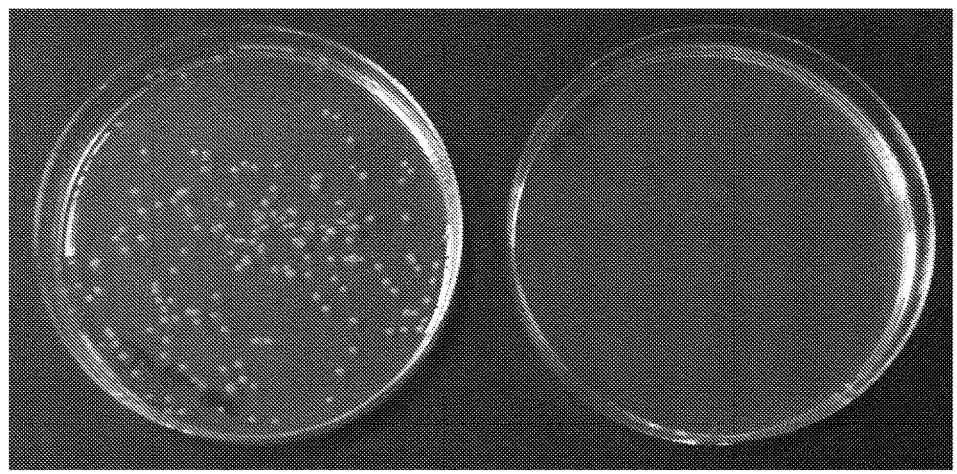
FIG. 4 shows antimicrobial cellulose untreated (left) and treated (right), 0.5 ml plated plated on Petri dishes.

The test was repeated using the same stock of bacteria juice (stored at 4° C.) with the following modifications: first, an additional brand of cellulose matrix which claims to be antimicrobial. Second, bacteria juice post overnight incubation was diluted 1:10 with sterile water. Third, two volumes, 0.5 ml and 0.1 ml, were plated and allowed to grow overnight (see Table 6; FIGS. 1-3).

TABLE 6

| Sponge type | Untreated (CFU) | Treated (CFU) |
|---|---|---|
| Cellulose, 0.1 ml | 1264 | 0 |
| Cellulose, 0.5 ml | 2832 | 0 |
| Antimicrobial cellulose, 0.1 ml | 75 | 0 |
| Antimicrobial cellulose, 0.5 ml | 175 | 0 |

Thus, the physical incorporation and thus compositing into the cellulose matrix insoluble antimicrobial composite was over ten times more effective than the "antimicrobial sponge." In addition, the poor performance of the "antimicrobial sponge" was rescued by compositing into the cellulose of insoluble antimicrobial, in this example copper.

Example 3

Figure 5:
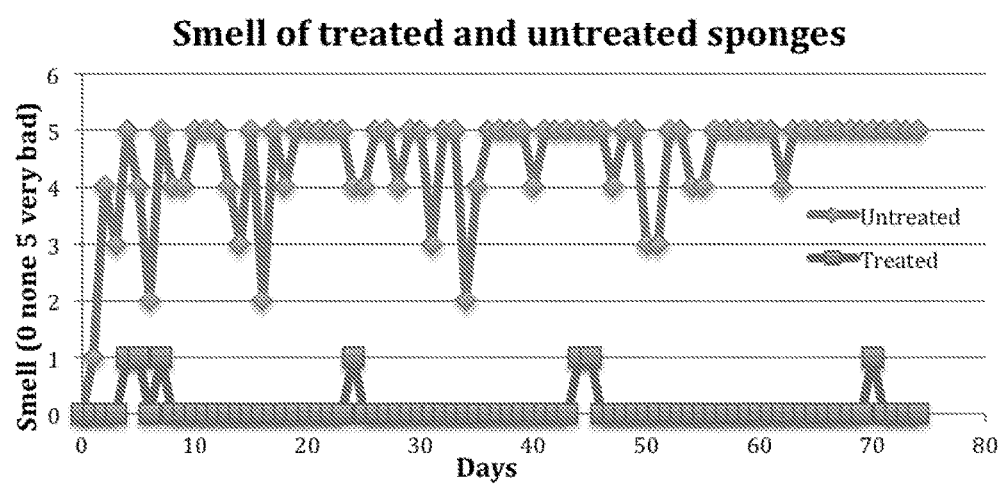
FIG. 5 shows a graph of smell of treated and untreated porous matrices.
Figure 6:
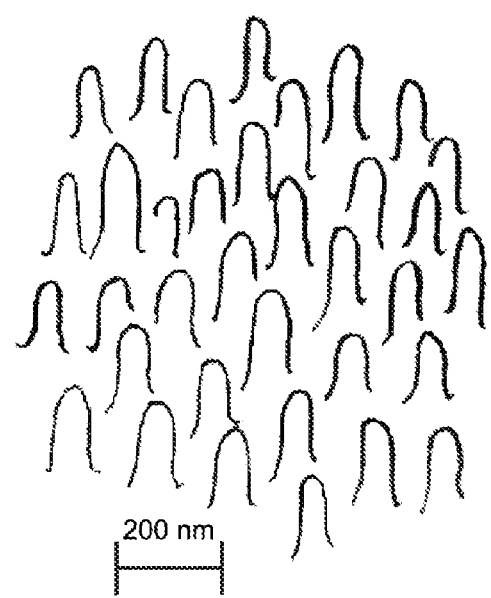
FIG. 6 shows a nano-piller afforded porous matrix composite with a close up view of the nanopillar surface of the porous matrix composite.

To further test the performance of the porous absorbent insoluble antimicrobial composite, a porous insoluble-antimicrobial matrix composite of cellulose and copper and an uncomposited porous cellulose matrix from the same manufacturer and batch was placed in a kitchen sink for over two months. Smell was rated on a scale from 0 (no smell or the smell only of food) to 5 (very bad). Both samples were exposed to identical conditions. These conditions included both those that could significantly reduce bacteria load (e.g. exposure to boiling water from for example pasta preparation or similar; doing dishes with very hot water; or exposure to cleaning with bleach) as well as conditions that could foster bacteria load (e.g. clean up after preparation of meat or fish; or cleaning of containers in which food spoiled). The uncomposited matrix consistently smelled much worse than the antimicrobial composite (see FIG. 5).

The same porous matrices (both composited and control uncomposited) as tested previously were assayed for performance over time as follows: both composite and control matrices were used as normal in cleaning and left damp in the bottom of the sink. Once per week at the end of the day, both composited and control uncomposited samples were washed of major food particles and isolated from additional use by placement in Ziploc bags. After overnight incubation at room temperature (on the counter top next to the sink to ensure the same temperature as the sink), bacteria juice from within the pores of each sample was taken by squeezing the pores matrices and filtered as described above. Bacteria juice was diluted 1:1000 in sterile water and 0.5 ml was plated. It is noted that in the absence of a proper linear-flow sterile hood, airborne environmental contamination can also be a contributing source of bacteria in the plates (see Table 7).

TABLE 7

| End of week | Untreated (CFU) | Treated (CFU) |
|---|---|---|
| 1 | 2483 | 0 |
| 2 | 5916 | 12 |
| 3 | 784 | 0 |
| 4 | Uncountable lawn | 25 |
| 5 | 2603 | 0 |
| 6 | 3935 | 0 |
| 7 | 683 | 0 |

Example 4

The incorporation of copper and, by extension, other solid antimicrobials (for example other metals like silver), into a larger volume production procedure of a flexible porous antimicrobial matrix composite was tested. A viscose/copper powder mixture was created by combining 300 g of copper powder with 400 kg of viscose, even mixing in rotary drums, combining this mixture with a pore-forming substance (in this case sodium sulfate crystals) to form pores, pouring the salt/viscose/copper mix into molds, solidifying the mixture with electrical current and washing the resultant pore-forming substance to result in a porous solidified matrix. A control batch was identically made but uncomposited (i.e. lacking insoluble antimicrobial here copper). The resulting products were washed as described above and tested as described similar to the above experiments: a cellulose matrix was left at the bottom of the sink, bacteria juice from the u composited matrix was squeezed out, this juice was coarsely filtered to remove food particles, the juice was poured into composited and uncomposited (control) solidified matrices and in this case was left for exactly 1 hr at room temperature. After exactly 1 hr, the composited and uncomposited matrices were squeezed out, the resultant juices were diluted 1:3000 and 0.1 ml was plated on LB plates. After ON growth at 37 C, the following colonies were counted (see Table 7):

TABLE 8

| Untreated (CFU) | Treated (CFU) |
|---|---|
| 804 | 1 |

Accordingly, flexible porous antimicrobial matrix composites manufactured in production scale procedures exhibit similar antimicrobial properties to those made in other manners.

Example 5

Copper and/or silver as a non-soluble, non-leaching antimicrobial is formed such that particles ≤10 micrometers in diameter bearing blunt spikes spaced approximately 0.5-200 micrometers apart on their exterior roughly biomimicking cicada wings; they might also be porous with spikes internal to their pores. These particles are added to cellulosic viscose, evenly distributed using a drum mixer and sodium sulfate crystals with a minimum average dimension of 1 mm across are added. This mixture is again mixed until all components are evenly distributed, the mixture is molded, the matrix is solidified, the pore-forming substance is removed, any non-physically bound non-leaching antimicrobial is removed, the product is washed and packaged. The resultant porous absorbent non-leaching antimicrobial matrix composite exhibits stronger antimicrobial effect than spheres of the same dimension.

Example 6

A porous solid cellulosic matrix (either natural *Luffa* or processed porous cellulose) is activated with thionyl chloride or other coupling agents to make produce intermediates which are exposed to anti-microbial peptides especially but not limited to G3KL (sequence $(KL)_8(KKL)_4(KKL)_2KKL$) and G3RL (sequence $(RL)_8(KRL)_4(KRL)_2KRL$) and/or their dendrimers, these peptides being synthesized from amino acids in D-stereoisomers to prevent protease activity. The resultant porous absorbent non-leaching antimicrobial matrix composite exhibits strong long-lasting antimicrobial effect and degrades very slowly.

Example 7

A porous solid cellulosic matrix (either natural *Luffa* or processed porous cellulose) is activated with thionyl chloride or other coupling agents to make produce intermediates which are exposed to amine-containing antimicrobials such as amino-quaternary amines, which are reacted such that >50 molecules are covalently anchored per cubic millimeter of the porous matrix, and unreacted molecules are removed. The resultant porous absorbent non-leaching antimicrobial matrix composite exhibits strong long-lasting antimicrobial effect and degrades very slowly.

The foregoing descriptions of specific embodiments of the present application have been presented for purposes of illustration and description. They are not intended to be exhaustive or to limit the application and method of use to the precise forms disclosed. Obviously many modifications and variations are possible in light of the above teaching. It is understood that various omissions or substitutions of equivalents are contemplated as circumstance may suggest or render expedient, but is intended to cover the application or implementation without departing from the spirit or scope of the claims of the present application.

What is claimed is:

1. A method of manufacturing an absorbent non-leaching antimicrobial porous matrix composite, comprising:
    making or obtaining a flexible porous solid matrix substrate that forms a pore-containing solid matrix, wherein the pores of the flexible porous solid matrix substrate have an average size of under 3 mm in width at their narrowest dimension;
    physically incorporating a non-leachable antimicrobial within or upon a pore-containing solid matrix, wherein the pore-containing matrix comprises a plurality of matrix pores, wherein each matrix pore comprises an interior, and wherein the non-leachable antimicrobial has exposure to the interior of the matrix pores;
    removing any non-physically incorporated non-leachable antimicrobial from the pore-containing solid matrix,
    wherein the non-leachable antimicrobial is physically incorporated within the pore-containing solid matrix by the step comprising:
    mixing the non-leachable antimicrobial with a solidifiable matrix in flowable form with a removable pore-forming substance,
    wherein the surface area to volume ratio of non-leachable antimicrobial is greater than 6000:1 $m^{-1}$ prior to compositing,
    and wherein the non-leachable antimicrobial is evenly distributed and physically enveloped within the solidifiable matrix,
    and wherein the solidifiable matrix is solidified while physically enveloping the pore-forming substance and the non-leachable antimicrobial to form the pore-containing solid matrix, and wherein the non-leachable matrix antimicrobial represents <5% wt/wt of a dried form of the absorbent non-leaching antimicrobial porous structure composite.

2. A method of manufacturing an absorbent non-leaching antimicrobial porous matrix composite, comprising:
    making or obtaining a flexible porous solid matrix substrate that forms a pore-containing solid matrix, wherein the pores of the flexible porous solid matrix substrate have an average size of under 3 mm in width at their narrowest dimension;
    physically incorporating a non-leachable antimicrobial within or upon a pore-containing solid matrix, wherein the pore-containing matrix comprises a plurality of matrix pores, wherein each matrix pore comprises an interior, and wherein the non-leachable antimicrobial has exposure to the interior of the matrix pores;
    removing any non-physically incorporated non-leachable antimicrobial from the pore-containing solid matrix, wherein the non-leachable antimicrobial is physically incorporated within or upon the pore-containing solid matrix by the step comprising:
    physically chemically covalently attaching the non-leachable antimicrobial to the solid matrix,
    wherein the physically chemically covalently attached non-leachable antimicrobial is uniformly attached to the surface of the pores and irregularities of the solid matrix,
    and wherein the non-leachable antimicrobial represents <2.5% wt/wt of a dried form of the absorbent non-leaching antimicrobial porous structure composite;
    and further wherein at least 50 molecules of the non-leachable antimicrobial are anchored per cubic millimeter.

3. The method of claim 1, wherein the solidifiable matrix in flowable form comprises one or more of polysaccharide, cellulose, viscose, non-natural polymers, thermosetting polymers, rubber (natural or artificial), and/or polymers based on acrylonitrile and styrenebutadiene.

4. The method of claim 1, wherein the removable pore-forming substance comprises one or more of sodium sulfate or salts, sugars, dissolvable natural polymers, or dissolvable artificial polymers.

5. The method of claim 1, wherein the pores in the pore-containing solid matrix have an average size of under 2 mm in diameter at their narrowest dimension.

6. The method of claim 1, wherein the pores in the pore-containing solid matrix have an average size of under 1 mm in diameter at their narrowest dimension.

7. The method of claim 1, wherein the non-leachable antimicrobial is selected from the group consisting of one or more of copper, silver, zinc, bismuth, gold, aluminum, boron, selenium, gallium, sulfur, germanium, barium, manganese, vanadium, lead, beryllium, cadmium, chromium, arsenic, tellurium, mercury, thallium, uranium, tin, antimony, indium, iron, cobalt or nickel, strontium, scandium, titanium, manganese, yttrium, zirconium, niobium, molybdenum, technetium, ruthenium, rhodium, palladium, lanthanum, hafnium, tantalum, tungsten, rhenium, osmium, iridium, platinum, gold, mercury, actinium, rutherfordium, dubnium, seaborgium, bohrium, hassium, meitnerium, darmstadtium, roentgenium, copernicium, cerium, praseodymium, neodymium, promethium, samarium, europium, gadolinium, terbium, dysprosium, holmium, erbium, thulium, ytterbium, lutetium, thorium, protactinium, uranium, neptunium, plutonium, americium, curium, berkelium, californium, einsteinium, fermium, mendelevium, nobelium, and lawrencium.

8. The method of claim 7, wherein a non-leachable antimicrobial selected from the group is sulfur.

9. The method of claim 2, wherein the pores in the pore-containing solid matrix have an average size of under 2 mm in diameter at their narrowest dimension.

10. The method of claim 2, wherein the pores in the pore-containing solid matrix have an average size of under 1 mm in diameter at their narrowest dimension.

11. The method of claim 2, wherein the non-leachable antimicrobial is selected from the group consisting of one or more of copper, silver, zinc, bismuth, gold, aluminum, boron, selenium, gallium, sulfur, germanium, barium, manganese, vanadium, lead, beryllium, cadmium, chromium, arsenic, tellurium, mercury, thallium, uranium, tin, antimony, indium, iron, cobalt or nickel, strontium, scandium, titanium, manganese, yttrium, zirconium, niobium, molybdenum, technetium, ruthenium, rhodium, palladium, lanthanum, hafnium, tantalum, tungsten, rhenium, osmium, iridium, platinum, gold, mercury, actinium, rutherfordium, dubnium, seaborgium, bohrium, hassium, meitnerium, darmstadtium, roentgenium, copernicium, cerium, praseodymium, neodymium, promethium, samarium, europium, gadolinium, terbium, dysprosium, holmium, erbium, thulium, ytterbium, lutetium, thorium, protactinium, uranium, neptunium, plutonium, americium, curium, berkelium, californium, einsteinium, fermium, mendelevium, nobelium, and lawrencium.

12. The method of claim 11, wherein a non-leachable antimicrobial selected from the group is sulfur.

* * * * *